(12) United States Patent
Lindkvist

(10) Patent No.: US 10,957,220 B2
(45) Date of Patent: Mar. 23, 2021

(54) SYSTEMS AND METHODS FOR ENDOVASCULAR FLUID INJECTION SIMULATIONS

(71) Applicant: Mentice, Inc., Evanston, IL (US)

(72) Inventor: Johan Lennart Lindkvist, Skene (SE)

(73) Assignee: MENTICE, INC., Chicago, IL (US)

( * ) Notice: Subject to any disclaimer, the term of this patent is extended or adjusted under 35 U.S.C. 154(b) by 476 days.

(21) Appl. No.: 16/019,370

(22) Filed: Jun. 26, 2018

(65) Prior Publication Data

US 2018/0374390 A1   Dec. 27, 2018

Related U.S. Application Data

(60) Provisional application No. 62/525,138, filed on Jun. 26, 2017.

(51) Int. Cl.
*G09B 23/28* (2006.01)
*A61M 5/00* (2006.01)
*A61M 5/178* (2006.01)
*G09B 23/30* (2006.01)

(52) U.S. Cl.
CPC ........... *G09B 23/285* (2013.01); *A61M 5/007* (2013.01); *A61M 5/178* (2013.01); *G09B 23/303* (2013.01)

(58) Field of Classification Search
CPC .... G09B 23/285; G09B 23/303; A61M 5/007; A61M 5/178

USPC ........................................................ 434/262
See application file for complete search history.

(56) References Cited

U.S. PATENT DOCUMENTS

| 3,520,071 A | 7/1970 | Abrahamson |
| 5,284,423 A | 2/1994 | Holdsworth |
| 5,769,641 A | 6/1998 | Lampotang |
| 2013/0323700 A1 | 12/2013 | Samosky |

FOREIGN PATENT DOCUMENTS

WO   2017123655 A1   7/2017

OTHER PUBLICATIONS

European International Search Report for PCT/US2018/039597 dated Sep. 7, 2018.

*Primary Examiner* — Robert P Bullington
(74) *Attorney, Agent, or Firm* — Bryan Cave Leighton Paisner, LLP

(57) ABSTRACT

Systems and methods for simulating fluid injection procedures are disclosed. According to some embodiments, a fluid injection simulation system comprises a processing unit coupled to a variable flow resistance module. The processing unit determines a fluid flow resistance that corresponds to a predetermined level of resistance for tactilely simulating a fluid injection procedure. The processing unit controls the variable flow resistance module to achieve the fluid flow resistance that corresponds to the predetermined level of resistance for tactilely simulating a fluid injection procedure.

25 Claims, 7 Drawing Sheets

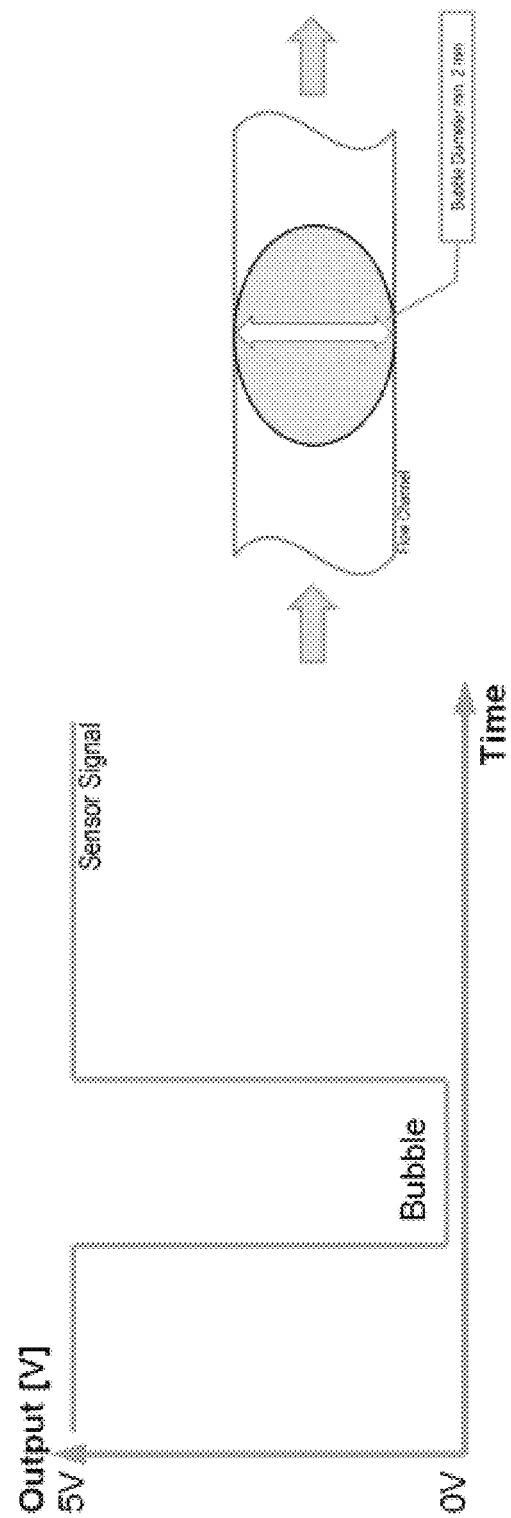

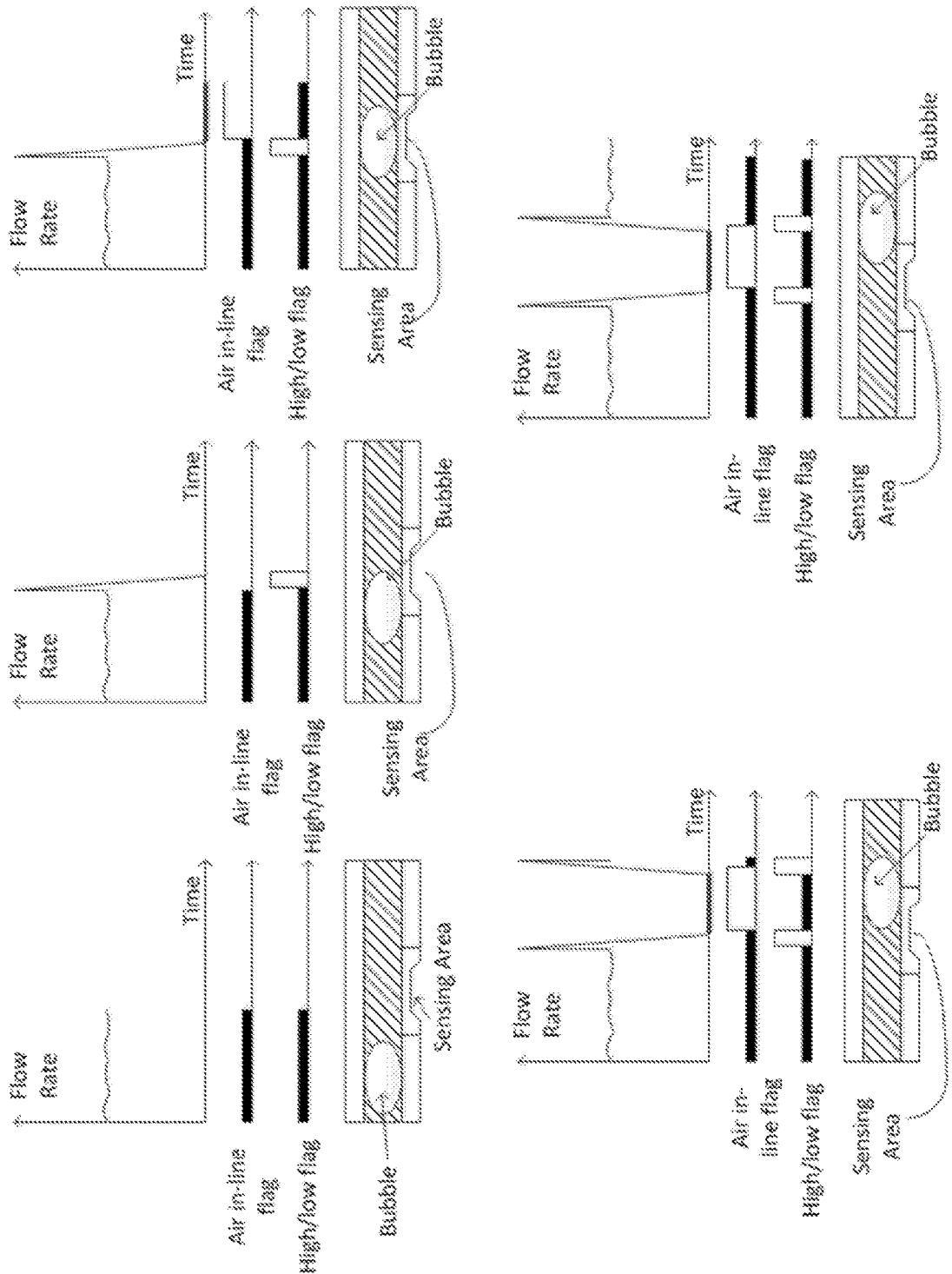

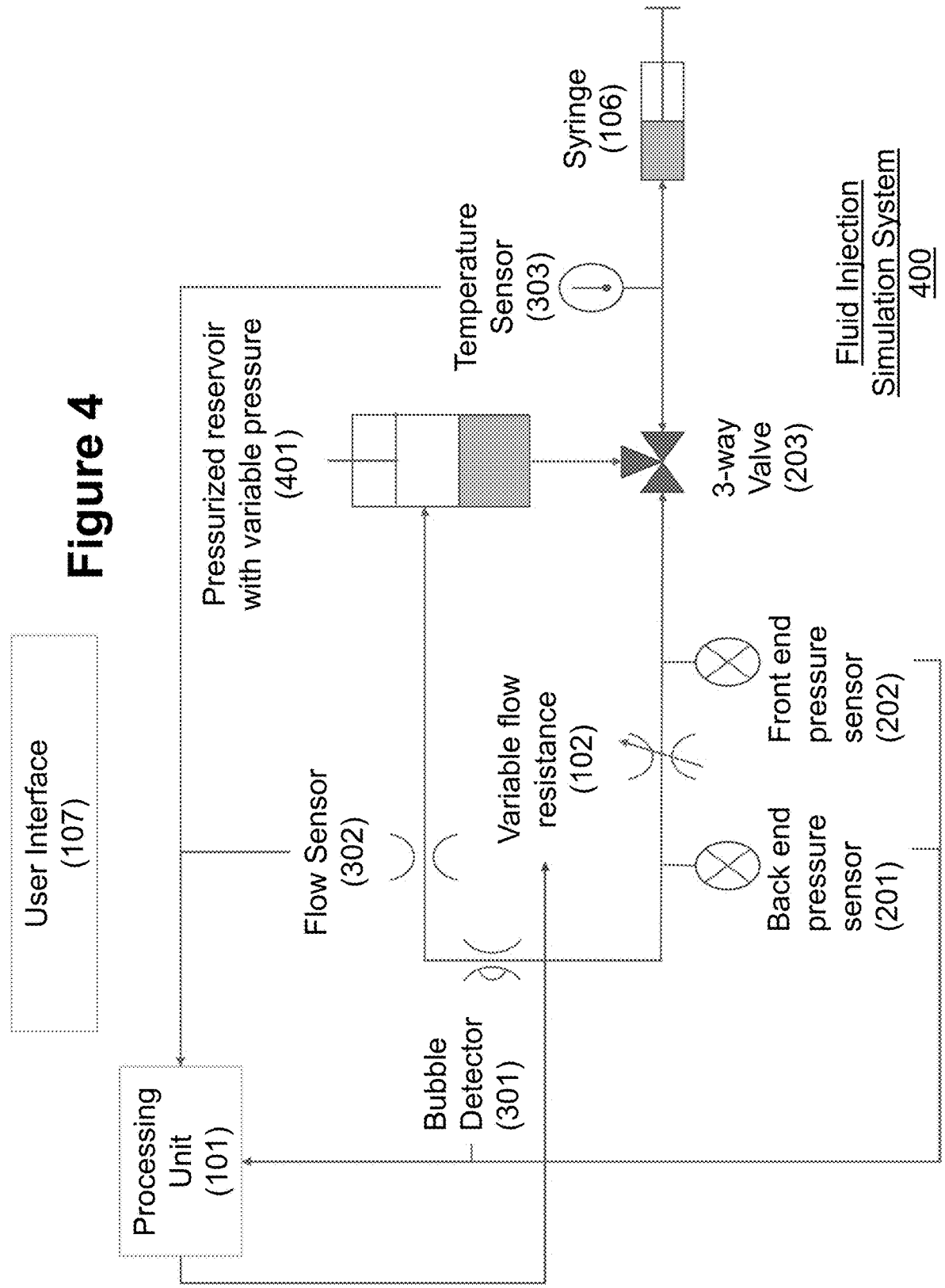

SYSTEMS AND METHODS FOR ENDOVASCULAR FLUID INJECTION SIMULATIONS

CROSS-REFERENCE TO RELATED APPLICATIONS

The present application claims priority to U.S. Provisional Patent Application No. 62/525,138 filed on Jun. 26, 2017, which is incorporated herein by reference in its entirety.

FIELD OF THE INVENTION

The invention is related to systems and methods for providing fluid injection and aspiration simulation, and in particular for simulating fluid injections and aspiration used with syringes, power injector, catheters, and balloons in the simulation of endovascular medical procedures.

BACKGROUND OF THE INVENTION

Fluid injection procedures involving syringes are used in a wide array of endovascular procedures, such as for example, contrast injection, embolic agent injection, saline injection, or balloon inflation. Thus, systems and methods for realistically simulating such fluid injection procedures have become increasingly important in training and honing the skills of medical practitioners. In such settings, fluid injection simulation systems can be used to assess or measure the performance of how a particular procedure is performed. Fluid injection simulation systems also play an important role in planning specific procedures, or objectively recommending particular tools or approaches based on given input data. A high fidelity fluid injection simulation system typically aims to simulate a real-world syringe injection as realistically as possible. Providing an accurate level of resistance and correctly estimating the amount of injected or aspirated fluid are both important for achieving a fully realistic simulation.

Existing fluid injection simulation systems typically connect a standard syringe to a flow sensor that measures the amount of air that is pushed through the syringe. Such systems give an estimate of the injected volume of fluid (e.g., air), but will not provide the appropriate resistance or tactile feedback during injection, since every injection will feel the same, independent of simulated catheter length, diameter, or type of fluid. The same tactile feedback or resistance would be felt by the user if air was replaced with any other fluid in these types of simulation systems.

Other existing fluid injection simulation systems use nonstandard syringes, with an electrical sensor mounted on the plunger of the syringe to measure the amount of injected fluid, without using fluid in the syringe itself. Such systems are less realistic, and therefore less valuable as training tools, because the syringe itself differs from the syringes used in real procedures. Moreover, such fluid injection simulation systems do not provide different levels of resistance or tactile feedback in the syringe, and do not accurately represent the pressure-flow dynamics of a fluid-based circulatory system. Further, such solutions are not capable of detecting potential air bubbles introduced into the liquid, as no liquid is used.

Existing fluid injection simulation systems also suffer from additional drawbacks. Such simulation systems tend to have very limited flow and pressure ranges, and can include a large number of sensors that, when fed to a central processor, become computationally intensive to analyze. Further, such simulation systems tend to use flow sensors that rely on heating elements and temperature sensors that add to the overall expense, size, and processing power of the system, further rendering such simulation systems less compact, efficient, and useable by medical practitioners.

Existing simulation systems also do not measure the pressure that is effectively being sensed by the user or the pressure applied as he or she manipulates the syringe. Thus, the existing simulation systems do not provide a way to verify if the user is feeling or experiencing the amount of resistance or tactile feedback that it should be feeling or that the right level of pressure is being applied to the syringe. Measuring the amount of pressure being applied can be especially helpful in training users for certain applications. For example, some applications call for an injection rate that is so slow that it would be impractical for the operator to achieve such an injection rate by visually looking at the markings on the syringe. In these scenarios, an effective method of teaching users to control the flow of fluid at the correct injection rate is to train them to apply an appropriate and steady level of pressure and force. Measuring the amount of pressure being applied can also be helpful in detecting when the user is applying too much pressure such that it would present a risk of injuring tissue.

Further adding to the difficulty of realistically simulating a fluid injection procedure are the numerous factors that can change the pressure-flow dynamics of the circulatory system. For example, the simulation of a fluid injection procedure can depend on the amount and rate of fluid injected by a syringe, the type of syringe being used, the viscosity of fluid being injected, the length and diameter of the catheter that the fluid is being injected through, the placement of the catheter in the patient, and whether the tip of the catheter is adjacent to an object in the patient. Measuring and monitoring such factors can require incorporating additional sensors and subsystems that significantly add to the overall size, cost, and mobility of the system. Omitting such sensors prevent the simulation system from taking into account the factors that impact pressure-flow dynamics, and result in less accurate simulation of the actual resistance perceived by the user in the syringe. Existing systems for simulating syringe injections typically only measure one parameter (flow volume or rate), and do no simulate resistance. The accuracy of this measurement depends on the accuracy of that single flow sensor. Moreover, some existing systems are deficient in their accuracy of estimating fluid flow rates. Further, existing systems do not provide the ability to detect air bubbles during an injection.

Accordingly, there is a need for a compact, low-cost medical training system that can simulate fluid injection procedures by providing accurate tactile feedback based on the various factors that can impact the fluid's flow in the injection system, such as for example, the viscosity of the fluid, type of liquid being used, the length and diameter of catheter being used, and the presence of any obstructions. Further, there is a need to provide a fluid injection simulation system that can realistically simulate the level of resistance felt or perceived by a user based on accurate measurements of the pressure-flow dynamics of a fluid circulatory system. Still further, there is a need to provide a fluid injection simulation system that can operate in perfectly dry contexts where liquids cannot be used.

SUMMARY OF THE INVENTION

Methods and systems for simulating fluid injection procedures are disclosed. The methods and systems disclosed enable a user to realistically simulate a fluid injection procedure by controlling the flow resistance of a fluid flowing through a fluid injection system, and using components and instruments that are used in real-life medical procedures, such as for example, medical grade syringes, and fluids such as saline solution or blood. The fluid flow resistances are set at levels that correspond to the appropriate level of resistance that a user would tactilely feel when manipulating a syringe during a fluid injection procedure. The methods and systems disclosed provide improved accuracy and realistic simulations by using sensors to monitor instantaneous fluid flow rates.

According to some embodiments, a fluid injection simulation system can include a processing unit and a variable flow resistance module. The variable flow resistance module can be coupled to the processing unit. The processing unit determines a fluid flow resistance that corresponds to a predetermined level of resistance for tactilely simulating a fluid injection procedure. The processing unit controls the variable flow resistance module to achieve the fluid flow resistance that corresponds to the predetermined level of resistance for tactilely simulating a fluid injection procedure. Thus, the processing unit can be configured to control the variable flow resistance module to achieve a fluid flow resistance that corresponds to a predetermined level of resistance. In this way, the fluid injection simulation system can control the fluid flow resistance to create the appropriate resistance and tactile feedback that will be perceived by a user manipulating the syringe.

According to some embodiments, a fluid injection simulation system can include a valve, a reservoir for holding fluid, and a syringe The valve can be coupled to the variable flow resistance module through a first tube conduit. The syringe can be coupled to the valve through a second tube conduit. The reservoir can be coupled to the variable flow resistance module through a third tube conduit. A fluid flows through the variable flow resistance module, the valve, the syringe and the reservoir. The valve can be configured as a switch to open and close the flow of fluid from the syringe into the fluid injection simulation system.

In some embodiments, the fluid flow rate is calculated based on pressure-flow dynamics of the fluid injection simulation system. The fluid flow resistance can be static or time varying. For example, the amount of predetermined fluid flow resistance can be chosen to be static, i.e., fixed over time, so that the tactile feedback experienced by the user is substantially constant during the procedure. There are, however, some simulation scenarios where the fluid flow resistance can be time varying, and dynamically change over time. For example, the fluid flow resistance can vary over time to tactilely simulate a fluid injection procedure of a balloon. When a balloon is first being filled with fluid, there is relatively low resistive feedback. But, as the balloon expands and begins to reach capacity, the balloon becomes harder to inflate and provides an increasing amount of resistive feedback. Thus, the resistance perceived by the user can change as he or she manipulates the syringe, causing the pressure-flow dynamics of the system to change.

In some embodiments, the variable flow resistance module includes a two-way proportional needle valve that includes a linear actuator. The linear actuator can be controlled by a stepper motor that is pulsed to drive the linear actuator to control the flow of the fluid through the two-way proportional needle valve. In some embodiments, the fluid injection simulation system can include a stepper-controlled proportional valve driver configured to provide control signals for driving the stepping motor at a desired stepping rate. In some embodiments, the variable flow resistance module further comprises a piezoelectric proportional valve instead of a two-way proportional needle valve to control the fluid flow resistance.

In some embodiments, the syringe can be a medical-grade syringe for use in real-life procedures. In this way, the fluid injection simulation system can realistically simulate how a fluid injection procedure would feel with the type of syringe that would be used during a real-life procedure.

Similarly, in some embodiments, the fluid injection simulation system is capable of simulating fluid that is saline solution, contrast fluid, liquid embolics, or blood. Thus, unlike conventional simulation systems, the fluid injection simulation system can realistically simulate the pressure-flow dynamics of a fluid injection procedure using the type of liquid that would be used in that procedure.

In some embodiments, the fluid injection simulation system is capable of using a gas as the fluid. In this way, the fluid injection system can be used in environments that must be kept dry.

In some embodiments, the processing unit is configured to simulate an obstruction in a patient or medical equipment. The obstruction can be simulated by sending control signals to the variable flow resistance module to achieve a desired fluid flow resistance corresponding to the simulated obstruction.

In some embodiments, the fluid injection simulation system can include one or more pressure sensors. The processing unit can calculate a pressure difference over the variable flow resistance module based on measurements provided by the one or more pressure sensors. The processing unit can then calculate a volumetric flow rate based on the measured pressure difference. In some embodiments, the processing unit changes the desired fluid flow resistance based on the measurements provided by the one or more pressure sensors. In this way, the fluid injection simulation system can accurately determine the flow rate of the fluid in the system and modify the fluid flow resistance when it does not match the desired fluid flow resistance. As a result, the fluid injection simulation system provides a more realistic level of resistance felt by the user manipulating the syringe.

In some embodiments, the valve can be a three way valve having an inlet port, an outlet port, and a supply port. The supply port can be coupled to a reservoir. In this way, the fluid injection simulation system can provide a closed loop system allowing for the syringe to be aspirated or refilled with liquid from the reservoir without having to detach the syringe from the fluid injection simulation system.

In some embodiments, the fluid injection simulation system can include a bubble detector. The bubble detector can be placed in line with a tube conduit, along the path where the injection flows when a device, such as a syringe, is injecting fluid into the system. The bubble detector can detect the presence of bubbles in the fluid, thereby enabling the system to simulate real-life fluid injection procedures where the introduction of air bubbles into the cardiovascular system presents a dangerous risk to a patient.

In some embodiments, the fluid injection simulation system can include a flow sensor configured to determine flow rates based on thermal mass flow measurements. The flow sensor can be placed in line with a tube conduit, along the path where the injection flows when a device, such as a syringe, is injecting fluid into the system. The flow sensor can be used to complement the other sensors in the system to improve the overall accuracy of flow rate measurements.

In some embodiments, the fluid injection simulation system can include a temperature sensor. In some embodiments it can be placed in between a valve and a device, such as a syringe, that injects fluid into the system. The temperature sensors can be configured to record fluid temperature measurements, which can be used by the processing unit to adjust its calculations for variations in fluid viscosity.

In some embodiments, the reservoir is a pressurized reservoir with variable pressure. The pressurized reservoir with variable pressure can vary the amount of pressure in the system, thereby enabling the processing unit to further control different fluid flow resistances. In this way, the fluid injection system can simulate active pressure characteristics that would result in liquid flowing in the reverse direction, such as for example, blood pressure and the elasticity of balloons used in certain procedures.

BRIEF DESCRIPTION OF THE FIGURES

The objects and features of the invention can be better understood with reference to the following detailed description and accompanying figures, in which like numerals represent the same or similar elements.

FIGS. 3A, 3B, and 3C shows examples of flow sensors and bubble detectors incorporated into a syringe simulation system according to certain embodiments of the invention.

FIG. 4 shows examples of pressurized reservoirs incorporated into a syringe simulation system according to certain embodiments of the invention.

DETAILED DESCRIPTION OF THE INVENTION

The invention described herein provides systems and methods for the realistic simulation of fluid injections. The system and methods may be used to train and certify professionals to improve the skills of medical professionals using fluid injection procedures to treat patients. Embodiments of the invention may also be used for therapeutic device design, development and testing.

Figure 1:
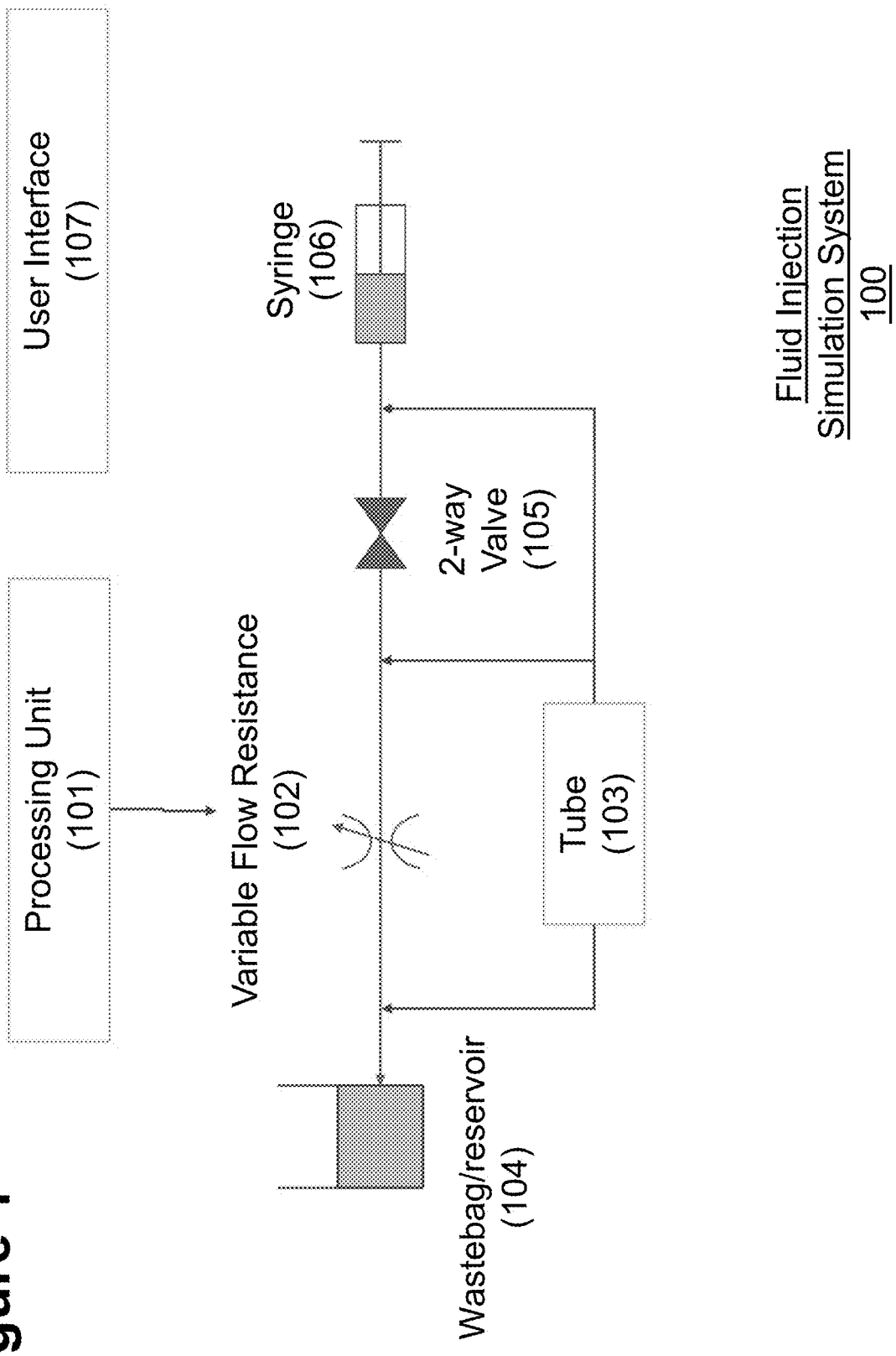
FIG. 1 shows examples of a syringe simulation system according to certain embodiments of the invention.

FIG. 1 shows examples of a fluid injection simulation system according to embodiments of the invention. The fluid injection simulation system can include a processing unit 101 coupled to a variable flow resistance module 102 for controlling the fluid flow resistance of the fluid running throughout tube conduits 103. In some embodiments, the variable flow resistance module 102 can be coupled to a reservoir 104 which stores the fluid that flows through the tube conduits 103. In some embodiments, the variable flow resistance module can be coupled to a valve 105 that controls the fluid flowing through its ports, thereby controlling the flow of the fluid through the overall fluid injection simulation system 100. In some embodiments, the valve 105 can be coupled to a device 106 that injects fluid into the fluid injection simulation system, such as for example, a syringe. In some embodiments, a user interface 107 can be coupled to the processing unit 101 to read and write data to the processing unit.

As explained in more detail below, processing unit 101 can determine the fluid flow resistance that corresponds to predetermined level of resistance for tactilely simulating a fluid injection procedure. The processing unit can send the appropriate control signals to the other components of the fluid injection simulation system, such as the variable flow resistance module, to achieve the fluid flow resistance that corresponds to the predetermined level of resistance for tactilely simulating a fluid injection procedure. The desired fluid flow resistance can be static (i.e., fixed), or time varying to emulate different fluid injection scenarios and the different behaviors of the various system components. Adjusting the fluid flow resistance changes the level of tactile feedback that is felt by the user and the resulting injection rate as he or she manipulates the syringe. In this way, the fluid injection simulation system can provide an enhanced level of realism to the simulation that incorporates the pressure-flow dynamics of the fluid injection or aspiration. In some embodiments described in more detail below, the fluid injection simulation system can include sensors that measure the actual flow rate of the fluid propagating through the system, and the pressure that is effectively being sensed by the user as he or she manipulates the syringe. The pressure that is effectively being sensed approximates the actual tactile feedback that is being experienced by the user, and should align with the predetermined level of resistance that tactilely simulates the fluid injection procedure. In some embodiments where the pressure being felt by the user does not match the predetermined level of resistance, the fluid injection simulation system can change the control signals being sent to the other system components so that the pressure being sensed by the user aligns with the predetermined level of resistance. In some embodiments, the pressure being sensed by the user can be used to determine if the user is applying too much pressure, which in some scenarios could be used to simulate a rupture in the blood vessel.

According to some embodiments of the invention, the processing unit determines the value of the various variables in the fluid injection simulation system that creates the desired effect perceived by a user. For example, the processing unit can determine a desired fluid flow resistance based on the type of simulation program being executed, such as a simulation of a blood clot stuck inside of a catheter. The predetermined fluid flow resistance can be pre-set and stored in a look-up table or as part of the simulation program that is downloaded onto the processing unit. For example, a simulation of a particular type of obstruction can be pre-set to have a predetermined fluid flow resistance, and stored in a look-up table or as part of the simulation program. The fluid flow resistance can also be calculated dynamically based on variables that are configurable by the user and other pressure-flow dynamics of the system. For example, the user can input through a user interface the type of syringe and tube conduit length or diameter being used in a simulation, and the processing unit or user interface can calculate the desired fluid flow resistance for that particular simulation. Other pressure-flow dynamics, including the amount and rate of fluid injected by a syringe, the viscosity of fluid being injected, the placement of the catheter in the patient, and whether the tip of the catheter is adjacent to an object in the patient, can be used to impact the fluid flow resistance.

The processing unit can provide the control signals to components in the fluid injection simulation system that achieve the desired effect. For example, the processing unit can send control signals to the variable flow resistance module, which it then uses to effectuate the fluid flow resistance. As explained in more detail below, the control signals can be, for example, the signals provided to a proportional valve driver that drives a stepping motor and actuator of a needle valve.

According to some embodiments, the processing unit can be coupled to a memory for storing and loading data. For example, as explained in more detail below, the processing unit can receive measurements from different components in the fluid injection simulation system, such as pressure sensors, and record the measurements in memory. The processing unit can load the saved measurements to perform pressure-flow dynamic calculations, such as volumetric flow rate of the fluid in the fluid injection simulation system. The data stored in the memory can also be stored for general data logging, so that a user can later load and view the different measurements that were recorded during a procedure.

In some embodiments, the processing unit comprises a microprocessor and the simulation programs can be loaded as firmware onto the microprocessor. The firmware can be loaded onto the microprocessor using a microcontroller programmer such as an AVR programmer and programming connector. The firmware can also be loaded through a bootloader over USB cables. The microprocessor can be 8-, 16-, 32-, or 64-bit microprocessors running at 8 MHz or faster. In some embodiments, the microprocessor can also include communication ports that enable communication of data to other components of the system. For example, the communication port can have a wireless transmitter that transmits data to other components such as a user interface. As another example, the connection port can have a USB-connection that transmits the data through a USB interface.

According to some embodiments of the invention, the variable flow resistance module includes driver, switching, and/or actuator elements which it controls based on the control signals received from the processing unit. For example, as described in more detail below, the variable flow resistance module can translate the control signals received from the processing unit into signals that drive a stepping motor and actuator that creates the desired fluid flow resistance.

According to some embodiments of the invention, the variable flow resistance module can include a two-way proportional needle valve having an inlet and outlet port through which the fluid flows. The two-way proportional needle valve can include a linear actuator controlled by a stepper motor. Depending on the desired fluid flow resistance determined by the processing unit and communicated to the variable flow resistance module, the stepper motor can be pulsed to drive a linear actuator including the needle, to control the flow of the fluid through the two-way proportional needle valve and the tube conduits it is connected to. The movement of the linear actuator can be changed to achieve a target fluid flow resistance. The two-way proportional needle valve can be coupled to a stepper-controlled proportional valve driver that receives power and control signals (e.g., step and direction), and produces signals for driving the stepper motor (e.g., OA to 2A in a bipolar stepper motor). The two-way proportional needle valve can thus be bidirectional, allowing fluid to flow in either direction through its ports. In some embodiments, the stepper-controlled proportional valve driver can provide the signals for driving the stepping motor at a desired stepping rate using a logic sequencer containing switching components, and a clock pulse source.

In some embodiments, the fluid injection simulation system can include a valve 105. Valve 105 can be a two-way valve that functions as a manual switch that either opens up or closes the flow from the syringe to the rest of the system. The two-way valve closes the flow of fluid when the syringe is disconnected, so that it may be refilled outside the system. Otherwise, the two-way valve can remain open. In some embodiments, the valve 105 can also be a three-way valve. A three-way valve can be used to open flow between the syringe and the reservoir to fill the syringe, and at the same time close the flow to the rest of the system, which represents the patient. When the syringe is filled, the valve can be manually turned to close the direct channel to the reservoir and open the direct channel to the rest of the system (the normal function of the three-way valve is to open two of the ports and close the third). In some embodiments, the fluid injection system may not include a valve 105, and the variable flow resistance module can be coupled directly to a syringe, power injector, or other device that injects fluid into the system.

In some embodiments, the resistance and tactile feedback is effectuated by setting a desired flow resistance in the variable flow resistance module 102. This simulates the expectations of medical practitioners performing real-life procedures, as they would expect to exert more force when pushing liquid through smaller catheters.

In some embodiments, calibration data can be stored as a lookup table within the processing unit, and used to convert the needle valve's position (i.e., how much it is open) into a flow resistance. In this way, a predetermined fluid flow resistance can be calibrated according to the particular simulation setup. In order to calculate volumetric flow rate, as described in more detail below, more than a single flow resistance value per needle valve position is needed. The calibration data thus stores a set of lines: two lines for each needle valve position of interest. The first line converts from positive pressure to flow rate, and the second from "negative" (below 1 atm) pressure to flow rate. Each row in the calibration table contains: needle valve position, $k_p$, $m_p$, $k_n$, $m_n$ where k and m represent the slope and the zero-crossing for the two lines.

According to some embodiments, variable flow resistance module 102 can be implemented with other mechanisms that control the fluid flow resistance of solution through a tube conduit. For example, the variable flow resistance module can include a solenoid, or electrical motor configured to clamp a tube, thereby restricting the flow of fluid in the tube conduit. The variable flow resistance module can also be used to control a piezoelectric proportional valve. The piezo elements of the piezoelectric proportional valve are electromechanical transducers that convert mechanical forces, such as for example, pressure, tensile stress or acceleration into a measurable voltage. A piezo element can also be deformed when it is subject to a voltage, thus generating mechanical motion or oscillations. A piezo element can include a capacitor having two electrically conductive plates and a ceramic piezo material which functions as a dielectric. The molecular structure of ceramic material in piezo elements becomes polarized when under the influence of electric fields. As a result, the ceramic material can change shape when subjected to a voltage.

The effect of changing shape when subjected to voltage can be leveraged with various types of transducers to create the piezoelectric proportional valve. For example, a piezo ceramic material that has conductive surfaces can be joined to a passive conductive substrate. Because the conductive surfaces of the piezo ceramic and substrate function as electrodes, the piezo ceramic material will bend when a voltage is applied to their conductive surfaces. The piezo ceramic material thus functions as a bender actuator, where the free end of the piezo ceramic material seals and opens a port valve as voltage is applied to the electrodes. Other examples of transducers include disc transducers and stack transducers, which similarly comprise ceramic material that expands and contracts when voltage is applied. One advantage of piezo elements is that they can be energized with minimal power, because the current flowing through the capacitor plates of the piezo element diminishes as the capacitor charges. As a result, the piezo element consumes little or no power when it is charged and no additional current flows through it. In comparison to other types of valves, proportional valves with piezoelectric components consume up to 95% less energy.

In some embodiments, the fluid injection simulation system can include a device 106 that injects fluid into the fluid injection simulation system, such as for example, a syringe. According to some embodiments, the syringe 106 can be an actual medical-grade syringe used in medical practice. Thus, unlike existing simulation systems, the fluid injection simulation system can realistically simulate the resistance and tactile feedback that would be perceived by a user during a real-life procedure. The syringe can also be a syringe that meets standard specifications and requirements used across hospitals and medical institutions. In this way, the syringe can be replaceable and provide maximum realism during a simulated procedure. The syringes can be disposable, and have various sizes, such as for example, 1 ml, 3 ml, 10 ml, 30 ml and 50 ml. In some embodiments, the device 106 that injects fluid into the fluid injection simulation system can be a power injector that can be programmed to automatically deliver specific amounts of fluid at specific flow rates. The power injector can be a real-life power injector as one would use in a real-life procedure, to enhance the realism of the simulation. The fluid injection simulation system can apply different fluid flow resistances depending on the mode of operation of the power injector being simulated an depending on different simulated scenarios controlled by the processing unit. In some embodiments, the fluid injection simulation system can be used to determine if the power injector has been configured correctly. For example, if the fluid injection simulation system determines that the measured pressure is maintained at a predetermined threshold, the fluid injection simulation system can determine that the power injector is correctly configured. The power injector can be used to both inject and aspirate fluid through the system. In some embodiments, the fluid injection system may not include a syringe or power injector 105, and the variable flow resistance module can be coupled directly to another device that facilitates the injection of fluid into the system.

When a user presses the syringe handle, the fluid in the syringe flows from its barrel through its tip and into the tube conduit, directing the overall flow of the fluid in the fluid injection simulation system towards the reservoir, through the variable flow resistance. The fluid flow rate will be determined by the pressure applied by the user via the syringe and the flow resistance applied by the processing unit. The fluid flow resistance set by the processing unit will affect the resistance and tactile feedback felt by the user and the resulting flow rate as he or she applies pressure to the syringe handle. Likewise, when the user pulls on the syringe handle, the fluid in the syringe flows from the reservoir and tube conduits into the direction of the syringe tip and into the syringe barrel. Similarly, the fluid flow resistance set by the processing unit will affect the resistance and tactile feedback felt by the user and the resulting flow rate as he or she pulls on the syringe handle. In this way, the fluid injection simulation system can be used to simulate both injection and aspiration.

In some embodiments, the fluid injection simulation system can include a reservoir 104. The reservoir 104 can be used to deposit and store the fluid flowing from the injection device 106 and through the fluid injection simulation system. The reservoir enables the fluid injection simulation system to provide a closed loop system allowing for the syringe to be aspirated or refilled with liquid from the reservoir without having to detach the syringe from the fluid injection simulation system. In real life procedures, a user would have to close the proximal valve after an injection, detach and remove the syringe, and have the syringe filled by a scrub nurse before re-attaching the syringe to the valve for a new injection. By using a closed loop system, the user can pull on the syringe to draw fluid from the reservoir instead of having to detach and remove the syringe. In some embodiments, the fluid injection system may not include a reservoir 104, and the variable flow resistance module can be coupled to other devices that will receive and/or direct the fluid flowing in the fluid injection simulation system.

The reservoir can be a fluid bag, waste bag, cup, bottle, or similar liquid container for holding fluids. The reservoir is coupled to the tube conduits through a port, from which the fluid flows to and from the reservoir. The reservoir can be re-usable and re-fillable, so that it can be used for multiple simulations. In some embodiments, the reservoir can be constructed of a material that is safe to machine-wash, thereby improving the reusability of the reservoir for additional simulations. The reservoir can be treated with coatings to accommodate various types of fluids and prevent corrosion or other types of damage that such fluids may cause. In some embodiments, the reservoir material can be constructed of materials that are chosen to withstand various pressures and temperatures of the fluids that are flowing through the system. In some embodiments, the reservoir can be encased in a protective casing. The protective casing can house the processing unit as well as other components of the system. In other embodiments, the reservoir can be kept apart from the processing unit or other components of the system. For example, the reservoir can be a hanging fluid bag hanging from a medical pole and kept uncased and apart from the processing unit.

According to some embodiments, different types of fluids can be simulated in the fluid injection simulation system to enable the simulation of different viscosities, flow resistances, and other behaviors of fluids. For example, the water or air can be used to simulate fluids such as saline solutions, contrast fluid, liquid embolics, blood, and different mixtures thereof. In some embodiments, the fluids and mixtures can be heated or cooled to desired temperatures to simulate real-world temperatures. The system can thus simulate the behaviors of different fluids that would be used in real-world settings between. For example, the system can simulate the overall tactile difference between using a syringe filled with contrast fluid and a syringe filled with blood. In some embodiments, the fluids used can be actual saline solutions, contrast fluid, liquid embolics, blood, and different mixtures thereof.

In some embodiments, the fluids can be a gas instead of a liquid. In this way, the fluid injection simulation system can be used in dry environments where liquids cannot be used. When gas is used instead of liquids, the air flow of the fluid is used in determining the measurements and calculations used by the other components of the fluid injection simulation system.

The fluids can flow into and out of reservoir 104 from tube conduits 103. Tube conduits can be medical grade tubing, such as luer tubes, constructed of plastic, silicon, latex, rubber, or similar materials. The tube conduits can be primed to prevent air from entering the fluid injection simulation system. Tube conduits can also be formed with various lengths and diameters. In this way, the system can be used to simulate fluid injections through different catheters within a single physical setup.

According to some embodiments, the system can be used to simulate various types of obstructions in a patient or medical equipment. For example, the system can be used to simulate a blood clot stuck inside of a catheter, a kink in a catheter, a catheter tip being heavily pressed against a vessel wall, a catheter deeply seated in a small vessel that cannot receive all the liquid injected, and similar types of obstructions. As explained in more detail below, these simulated obstructions can be selected by a user as a simulation program and loaded into the processing unit. The processing unit then determines the value of the various variables in the fluid injection simulation system that creates the desired effect for the selected simulation program. The processing unit then sends the control signals to those components in the fluid injection simulation system to achieve the desired effect. For example, if the user selected a simulation program that simulates a blood clot stuck inside of a catheter, the processing unit can send control signals to a variable flow resistance module to achieve the desired fluid flow resistance that would be experienced in such an obstruction. The simulation of the obstructions can account for other variables in the fluid injection simulation system, such as for example, the length and diameter of the tube conduits or type of injection fluid. Thus, the processing unit can adjust the control signals sent to the variable flow resistance module taking into account the length and diameter of the tube conduits or type of injection fluid being used.

Other events and behaviors can be simulated in a simulation program and executed by the processing unit to achieve desired effects. For example, a simulation program can simulate a blood vessel bursting by sending control signals to the variable flow resistance module to open rapidly at a given pressure.

In some embodiments, the processing unit can be programmed with predetermined thresholds for the different variables in the system. For example, the processing unit can be programmed with a max pressure guard. If the measured pressure reaches or exceeds the max pressure guard, the processing unit can control the variable flow resistance module to release the building pressure.

According to some embodiments of the invention, user interface 107 can be coupled to processing unit 101 for reading and writing data to and from the processing unit. The data can be, for example, the results of a recent simulation that were stored on the processing unit, and displayed for users to view. The data can also be a simulation program that specifies the value of the various variables in the fluid injection simulation system that creates the desired effect for a given simulation. For example, a simulation program can provide the desired fluid flow resistance to simulate a blood clot stuck inside of catheter, or the viscosity of a given contrast fluid. The simulation program can also include information about the fluid injection simulation system that can impact the injection of a fluid, such as for example, the length and diameter of the tube conduits. As explained above, the processing unit provides control signals to the different components in the fluid injection simulation system to achieve the desired effect based on the simulation program. For example, the processing unit can send control signals to a variable flow resistance module to achieve the desired fluid flow resistance specified in the simulation program. The user interface can display the various simulation programs for the user to select. When the user selects the desired simulation program, the simulation program can be loaded onto the processing unit.

According to some embodiments of the invention, the user interface can also be used to read and view data received and calculated by the processing unit. For example, the user interface can display the volumetric flow rates that the processing unit calculated in real time. As another example, the user interface can display a log of saved measurements and calculations that were stored over the course of a procedure.

Figure 2:
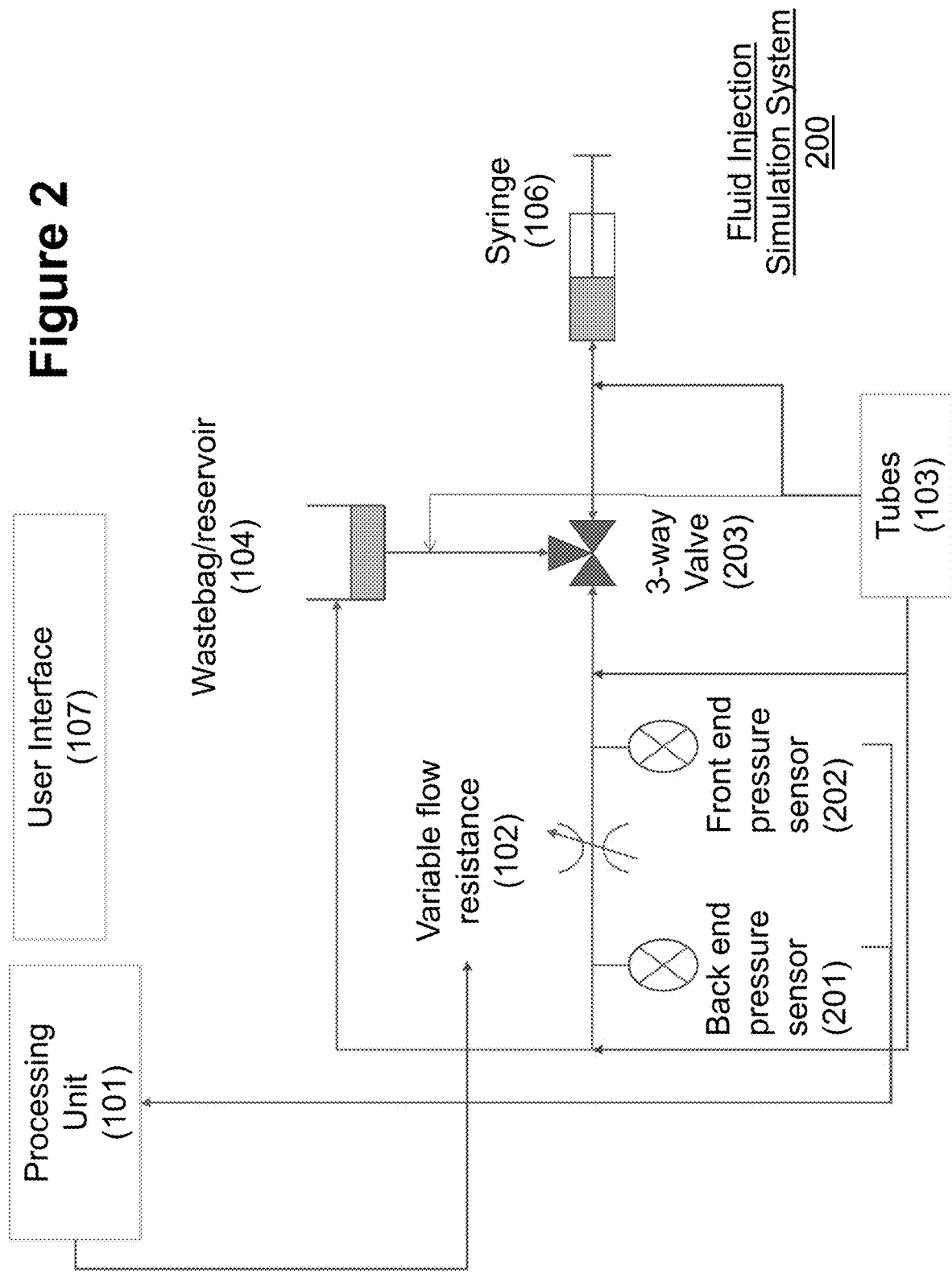
FIG. 2 shows examples of pressure sensors incorporated into a syringe simulation system according to certain embodiments of the invention.

FIG. 2 shows examples of a fluid injection simulation system according to embodiments of the invention using pressure sensors. As shown in FIG. 2, the fluid injection simulation system can include a processing unit 101 coupled to a variable flow resistance module 102, back-end pressure sensor 201 and front-end pressure sensor 202. The back-end pressure sensor 201 and front end pressure sensor 202 are placed on opposite sides of the variable flow resistance module 102, which controls the flow resistance of the fluid running throughout tube conduits 103. The variable flow resistance module 102 can be coupled to a reservoir 104 to store the fluid that flows through the tube conduits 103. The variable flow resistance module can control the fluid flow resistance flowing through its ports, thereby controlling the flow of the fluid through the overall system 200. The variable flow resistance module can be coupled to valve 203. The valve 203 can also be coupled to a device 106 that injects fluid into the fluid injection simulation system, such as for example, a syringe. In some embodiments, a user interface 107 can be coupled to the processing unit 101 to read and write data to the processing unit.

The back end pressure sensor 201 and front end pressure sensor 202 provide a pressure difference over the variable flow resistance module 102. Given the pressure difference over the variable flow resistance module, the flow through the valve and overall fluid injection simulation system can be determined.

For example, the flow can be estimated as the volumetric flow rate given by the Hagen-Poiseuille equations below and the assumption that the cross section of the conduit is circular.

$$\text{Volumetric Flow Rate} = \frac{P_1 - P_2}{R}$$

$$R = \frac{8nL}{\pi r^4}$$

R is the flow resistance combined with dynamic viscosity of a fluid in a conduit, $P_1$ and $P_2$ are measurements of the pressure of the fluid at two points along the conduit, r is the radius of the conduit, L is the length between the measurements of pressure along the conduit, and n is the viscosity of the fluid. The volumetric flow rate above is integrated over time by summing the above flow estimate and multiplying the sum by the sample interval, for all sample intervals. The pressure and flow rates can be measured and calculated in real-time. For example, the pressure and flow rates can be measured and calculated at a rate of 1 kHz.

In some embodiments, the fluid injection simulation system can estimate a flow rate using only one pressure sensor instead of two. For example, one of the two pressure sensors can measure the pressure of the fluid on one side of the variable flow resistance module while the pressure on the other side of the variable flow resistance module can be assumed as normal ambient air pressure, or another predetermined or known value. In yet other embodiments of the invention, pressure can be measured on one or both sides of the variable flow resistance module and complemented by one or more flow sensors for higher accuracy.

The back-end and front-end pressure sensors can be coupled to the processing unit to send the pressure measurements they have measured. The processing unit can use the pressure measurements to calculate volumetric flow rate in real time. The processing unit can also store the measurements in memory as a log for later usage or analysis.

With real-time calculations of pressure, the processing unit can ensure that the actual level of resistance as measured by the system sensors match the desired fluid flow resistance in real-time. For example, if the actual fluid flow resistance is less than the desired fluid flow resistance, the processing unit can send control signals to the variable flow resistance module to increase the fluid flow resistance. Likewise, if the actual fluid flow resistance is greater than the desired fluid flow resistance, the processing unit can send control signals to the variable flow resistance module to decrease the fluid flow resistance.

Front-end pressure sensor 202 and back-end pressure sensor 201 can be miniature board mounted sensors for measuring pressure. The pressure sensors can comprise sensing elements that cause a circuit element to vary based on pressure changes. For example, a sensing element can include piezo resistors on a chemically etched silicon diaphragm. A pressure change will cause a strain in the diaphragm and the resistors. The resistor values will change in proportion to the stress applied on the diaphragm, producing an electrical output signal commensurate with the pressure change.

According to some embodiments, the valve 203 can be a three-way valve. The third port of the three-way valve can be coupled to the reservoir 104, providing a direct supply of fluid to the valve. As described above, the three-way valve can allow the user to manually direct the flow of fluid through three ports. Turning or switching the three-way valve enables the use to either fill the syringe with liquids from the reservoir or discharge of excess fluid into the reservoir (corresponding to one position of the three-way valve), or to inject into/aspirate from the rest of the system represented by the flow resistance (corresponding to another position of the valve). Coupling the three-way valve to the reservoir allows the user to create a closed loop system and thereby refill or aspirate the syringe without detaching it from the valve.

Figure 3A:
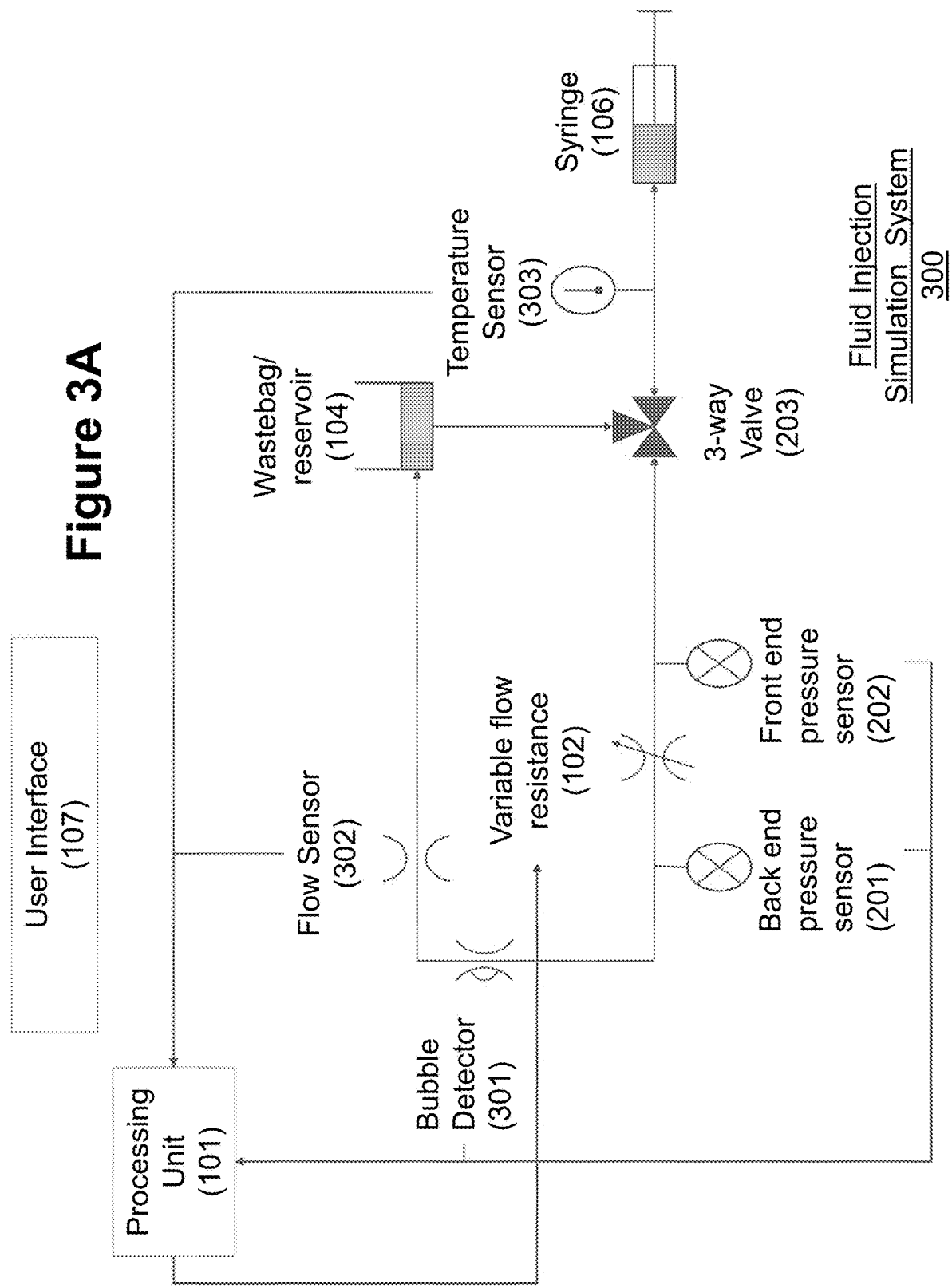

FIG. 3 shows examples of a fluid injection simulation system according to embodiments of the invention using bubble detectors and flow sensors. As shown in FIG. 3, the fluid injection simulation system can include a processing unit 101, variable flow resistance module 102, back-end pressure sensor 201, front-end pressure sensor 202, valve 203, device 106 that injects fluid into the fluid injection simulation system, such as for example, a syringe, and optionally a user interface 107. In some embodiments, the fluid injection simulation system can include a bubble detector 301, flow sensor 302, temperature sensor 303, or any combination thereof. The bubble detector 301 and flow sensor 302 can be placed in line with the tube conduit along the path by which fluid flows from the syringe. The temperature sensor can be placed in between the valve 203 and the device 106 that injects fluid into the fluid injection simulation system, such as for example, a syringe.

According to some embodiments, the bubble detector 301 is a sensor configured to determine the presence of air or bubbles in a liquid flowing through the tube conduits. The sensor can determine the presence of air or bubbles by detecting changes in the instantaneous flow rate, how long the instantaneous flow rate is at a certain threshold range, and whether the instantaneous flow rate exceeds a threshold level. For example, as shown in FIG. 3B, if the instantaneous flow rate instantaneously drops to zero for a certain window of time before returning to its prior flow rate, the bubble detector can determine that the change in rate was due to the presence of a bubble. According to some embodiments, the instantaneous flow rate signal can be compared to a library of bubble profiles. For example, as shown in FIG. 3C, when the instantaneous flow rate signal matches the profile of a bubble, the bubble detector can determine that a bubble is present in the tube conduit.

As explained in more detail below, the ability to detect bubbles can be useful in simulations because in real-life fluid injection procedures, the introduction of air bubbles into the cardiovascular system is dangerous and can increase the risk of creating air induced thromboses, which can lead to stroke. Thus, any bubbles detected by the bubble detector can be communicated to the processing unit for storage and analysis.

According to some embodiments, the flow sensor 302 is a sensor configured to determine flow rates based on thermal mass flow measurements. As explained above, such flow sensors are limited in their operable range, and typically operate within a few hundred µl/h to 1000 ml/h for example. However, such flow sensors can nevertheless be used to complement the other sensors in the system to improve the overall accuracy of flow rate measurements. For example, when the flow rates of the fluid injection simulation system are within the operable range of flow sensor 302, they can be used to cross-check the measurements and calculations generated by the pressure sensors.

According to some embodiments, the flow sensor 302 can include a heating element that adds a minimal amount of heat to the fluid for thermal flow measurement. Two temperature sensors, symmetrically positioned above and below the source of the heat, detect even slight temperature differences, thus providing the basic information about the spread of the heat, which itself is directly related to the flow rate.

According to some embodiments, the fluid injection simulation system includes a temperature sensor 303 that measures fluid temperature. The fluid temperature measurements can be used by the processing unit to adjust its calculations for variations in fluid viscosity. A temperature sensor may include thermistors, resistance temperature detectors, thermopiles, and similar semiconductor-based temperature sensors. In some embodiments, the temperature sensor 303 can include a humidity sensing element for measuring moisture. Measuring moisture would enhance the safety of the system by indicating whether a tube conduit is leaking. The temperature sensor and humidity sensor can be separate or combined into a singular package.

FIG. 4 shows examples of a fluid injection simulation system according to embodiments of the invention using a pressurized reservoir with variable pressure. As shown in FIG. 4, the fluid injection simulation system can include a processing unit 101, variable flow resistance module 102, back-end pressure sensor 201, front-end pressure sensor 202, valve 203, device 106 that injects fluid into the fluid injection simulation system, such as for example, a syringe, bubble detector 301, flow sensor 302, temperature sensor 303, a pressurized reservoir with variable pressure 401, and optionally a user interface 107.

The pressurized reservoir with variable pressure 401 can be coupled to the processing unit which provides controls signals that vary the amount of pressure applied to the reservoir. By increasing or decreasing the amount of pressure applied to the reservoir, the pressurized reservoir with variable pressure can further control different fluid flow resistances. In this way, the fluid injection system can simulate active pressure characteristics that would result in liquid flowing in the reverse direction, such as for example, blood pressure and the elasticity of balloons used in certain procedures. For example, because of the elasticity of a balloon, a balloon will naturally provide a reactive force against the force trying to inflate it, i.e., a syringe. As a balloon is filled, it will exert more reactive force against the syringe. As another example, under certain circumstances the blood will flow through a catheter in the reverse direction unless the correct amount of reactive force is present. The pressurized reservoir helps simulate these effects by providing the pressure that achieves the reactive force.

Figure 5:
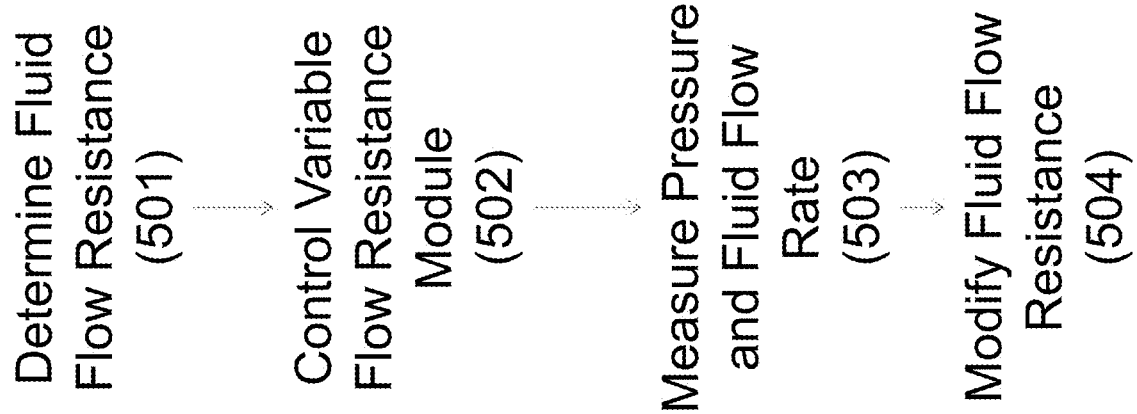
FIG. 5 shows examples of methods for using a syringe simulation system according to certain embodiments of the invention.

FIG. 5 shows examples of methods for using a syringe simulation system according to certain embodiments of the invention. The methods can include the step of determining a fluid flow resistance 501. As described above, the processing unit can determinate a fluid flow resistance that corresponds to the desired level of resistance or tactile feedback that will be perceived by the user manipulating the syringe. According to some embodiments of the invention, the processing unit determines fluid flow resistance based on the simulation program being executed by the user. For example, the processing unit can determine a desired fluid flow resistance for the simulation of a blood clot stuck inside of a catheter.

The methods can include the step of controlling a variable flow resistance module 502. As described above, the variable flow resistance module can be controlled by the processing unit through control signals that correspond to the desired fluid flow resistance that was determined in step 501. The control signals can be, for example, the signals provided to a proportional valve driver that drives a stepping motor and actuator of a needle valve, which pumps the fluid at the desired fluid flow resistance.

The methods can include the step of measuring a fluid flow rate 503. As described above, the fluid injection simulation system can include one or more pressure sensors that can be used to calculate the volumetric flow rate of the fluid passing through the valve. The pressure sensors can provide measurements to the processing unit, enabling it to calculate the instantaneous flow rates of the fluid passing through the valve and tube conduits in real-time.

The methods can include the step of modifying the fluid flow resistance 504. As described above, the real-time measurements of pressures, temperatures and estimates of fluid flow rates allows for the processing unit to ensure that the actual flow resistance as measured by the system sensors match the desired fluid flow resistance in real-time. For example, if the actual flow resistance is less than the desired fluid flow resistance, the processing unit can send control signals to the variable flow resistance module to increase the flow resistance. Likewise, if the actual flow resistance is greater than the desired fluid flow resistance, the processing unit can send control signals to the variable flow resistance module to decrease the flow resistance.

The systems and methods described herein can be used in medical training applications to provide several learning objectives. For example, a learning objective can be the ability to: avoid applying excessive pressure/flow with risk of dissection or rupture of blood vessel; adapt pressure/flow in relation to anatomy, pathology and patient condition in general; distinguish occlusion in a catheter and normal free flow and take the right measures in accordance therewith; recognize when catheter tip is occluded by vessel wall and show the ability to adapt pressure and/or position; distinguish no-flow, intermittent flow and continuous flow when aspirating; inject embolics with correct flow without exceeding pressure limits or burst limits of catheters; inject embolics with altering pressure/flow to change progression of embolics; correctly fill low-pressure balloons without exceeding burst pressure or max volume; and introduce air bubbles into the cardiovascular system avoiding the risk of creating air induced thromboses, which can lead to stroke.

Table 1 below shows examples of values of different pressure-flow dynamics and system variables for simulating various use case scenarios.

TABLE 1

Manual injection of contrast through devices ranging from inner lumen of balloon to 8-9F sheath with a syringe ranging from 1 ml to 20 ml

| | | | |
|---|---|---|---|
| Aorta/iliac (larger vessels och catheters, vessel diameter >8 mm, 6F and larger) | Flow range 3-5 ml/s | Syringe volume: 10-20 ml | Flow resistance (nominal): 1-2 bar*s/ml |
| Carotids/coronary ostia (medium sized vessels and devices, vessel diameter 3-8 mm, 3-6F), 1-3 ml/s | Flow range: 1-3 ml/s | Syringe volume: 5-10 ml | Flow resistance (nominal): 2-5 bar*s/ml |
| Coronaries/cerebrals/ATA (BTK) (smaller vessels and MC, balloons etc., vessel diameter <3 mm, 3F and smaller), <1 ml/s | Flow range: 0.2-1 ml/s | Syringe volume: 1-3 ml | Flow resistance (nominal): 5-100 bar*ml/s |

Manual aspiration in devices ranging from OD 3F aspiration catheters to ID 6F sheath

| | | | |
|---|---|---|---|
| | Flow range: 0.5-2 ml/s | Syringe volume: 20-50 ml | Flow resistance (nominal): 1-25 bar*s/ml |

Table 2 below shows examples of values of different system variables for simulating additional specific use case scenarios.

TABLE 2

| | | | |
|---|---|---|---|
| Manual injection of embolics through micro catheters with a syringe ranging from 1 to 3 ml | Flow range: 0.2-1 ml/min (Note: per minute), 2-8 atm | Syringe volume: 1-3 ml | Flow resistance (nominal): 500-1500 bar*s/ml |
| Manual filling of low pressure balloons, like occlusion balloons, cello | Flow range: 1-2 ml/min (Note: per minute) | Syringe volume: 1 ml | |

"Syringe volume" provides an indication of the reservoir needed. Pressures are normally between 0 and 10 atm, and max flow resistance can be modeled as infinity. Flow and resistance values are approximate and preferably should be used to obtain a view of the range(s) that are covered.

One exemplary procedure where the fluid injection simulation system can provide a realistic simulation of a real-life procedure, is with the treatment of Acute Ischemic Stroke. One type of treatment which has been shown to be effective is thrombectomy, which is an endovascular procedure. One critical component in such a procedure is to create a visualization of the blood vessels in the brain. This is done with a contrast injection, and it is very important that care is taken to apply the correct level of syringe pressure when injecting this fluid into the delicate blood vessel system of the brain, because using an incorrect level of syringe pressure can cause ruptures or other damage to the brain vessel.

Other applications that are particularly well suited for the aforementioned fluid injection simulation system include procedures that involve injecting embolization agents, such as for example in PAE (Prostatic Artery Embolization), TACE (Liver Embolization), or Vascular Trauma embolization. Other potential applications include balloon inflation, where the sensation of inflating a balloon (where the injection resistance increases with injected volume) can be simulated by the system using air instead of liquid. Balloon inflations are often used with for example REBOA, PCI, and pulmonary vein isolation procedures.

The systems and methods described above are particularly suited for simulating endovascular fluid injection procedures. An endovascular procedure is a minimally invasive, image guided procedure that uses medical instruments which are introduced into the blood vessels of the patient through an opening, typically in the groin, wrist or neck area, and their motion inside the body of the patient is visualized by the fluoroscope or x-ray system. It is therefore most useful for procedures within the fields of interventional cardiology, interventional radiology, vascular surgery, interventional neuroradiology, electrophysiology, structural heart disease, interventional oncology and cardiovascular surgery. However, the systems and methods described herein can be used for other procedures where fluid is injected into a patient.

The embodiments described in this disclosure can be combined in various ways. Any aspect or feature that is described for one embodiment can be incorporated into any other embodiment mentioned in this disclosure. Moreover, any of the embodiments described herein may be hardware-based, software-based and/or comprise a mixture of both hardware and software elements. Accordingly, while various novel features of the inventive principles have been shown, described and pointed out as applied to particular embodiments thereof, it should be understood that various omissions and substitutions and changes in the form and details of the systems and methods described and illustrated, may be made by those skilled in the art without departing from the spirit of the invention. Amongst other things, the steps of any described methods may be carried out in different orders in many cases where such may be appropriate. Those skilled in the art will recognize, based on the above disclosure and an understanding therefrom of the teachings of the inventive principles, that the particular hardware and devices that are part of the system described herein, and the general functionality provided by and incorporated therein, may vary in different embodiments of the inventive principles. Accordingly, the particular system components are for illustrative purposes to facilitate a full and complete understanding and appreciation of the various aspects and functionality of particular embodiments of the present principles as realized in system and method embodiments thereof. Those skilled in the art will appreciate that the inventive principles can be practiced in other than the described embodiments, which are presented for purposes of illustration and not limitation.

The invention claimed is:

1. A fluid injection simulation system comprising:
a processing unit;
a variable flow resistance module coupled to the processing unit;
wherein a fluid flows through the variable flow resistance module; and
wherein the processing unit is configured to control the variable flow resistance module to achieve a fluid flow resistance that corresponds to the predetermined level of resistance.

2. The fluid injection simulation system of claim 1 further comprising:
a valve coupled to the variable flow resistance module through a first tube conduit;
a syringe coupled to the valve through a second tube conduit;
a reservoir for holding fluid coupled to the variable flow resistance module through a third tube conduit;
wherein the valve is configured to open and close the flow of fluid from the syringe into the fluid injection simulation system; and
wherein the fluid flows through the variable flow resistance module, the syringe and the reservoir through the first, second and third tube conduits.

3. The fluid injection simulation system of claim 1 wherein a fluid flow rate is calculated based on pressure-flow dynamics of the fluid injection simulation system.

4. The fluid injection simulation system of claim 1 wherein the fluid flow resistance is one of static and time varying, wherein the time varying fluid flow resistance varies over time to tactilely simulate a fluid injection procedure of a balloon, and wherein the time varying fluid flow resistance varies over time based on calculations and determinations made by the processing unit.

5. The fluid injection simulation system of claim 1 wherein the variable flow resistance module further comprises a two-way proportional needle valve comprising a linear actuator controlled by a stepper motor, and wherein the stepper motor is configured to pulse to drive the linear actuator to control the fluid flow resistance.

6. The fluid injection simulation system of claim 2 wherein the syringe is detachable upon the valve being configured to close the flow of fluid from the syringe.

7. The fluid injection simulation system of claim 6 further comprising a stepper-controlled proportional valve driver configured to provide control signals for driving a stepping motor at a desired stepping rate.

8. The fluid injection simulation system of claim 1 wherein the variable flow resistance module further comprises a piezoelectric proportional valve to control the fluid flow resistance.

9. The fluid injection simulation system of claim 2 wherein the syringe is a medical-grade syringe for use in real-life procedures.

10. The fluid injection simulation system of claim 1 wherein the fluid injection simulation system is capable of simulating fluid that is saline solution, contrast fluid, liquid embolics, or blood.

11. The fluid injection simulation system of claim 1 wherein the fluid is a gas.

12. The fluid injection simulation system of claim 1 wherein the processing unit is configured to simulate an obstruction in a patient or medical equipment by sending control signals to the variable flow resistance module to achieve a predetermined level of resistance that tactilely simulates the obstruction.

13. The fluid injection simulation system of claim 1 further comprising a first pressure sensor, wherein the processing unit is configured to calculate a pressure difference over the variable flow resistance module based on measurements provided by the first pressure sensor.

14. The fluid injection simulation system of claim 13 wherein the processing unit is further configured to calculate a volumetric flow rate based on the pressure difference.

15. The fluid injection simulation system of claim 13 further comprising a second pressure sensor wherein the processing unit is configured to calculate a pressure difference over the variable flow resistance module based on measurements provided by the first pressure sensor and second pressure sensor.

16. The fluid injection simulation system of claim 13 wherein the processing unit is configured to change the fluid flow resistance based on measurements provided by the first pressure sensor.

17. The fluid injection simulation system of claim 2 wherein the valve is a three way valve having an inlet port, an outlet port, and a supply port, wherein the supply port is coupled to the reservoir through a fourth tube conduit.

18. The fluid injection simulation system of claim 13 further comprising a bubble detector and a flow sensor.

19. The fluid injection simulation system of claim 13 further comprising a temperature sensor.

20. The fluid injection simulation system of claim 2 wherein the reservoir is a pressurized reservoir with variable pressure.

21. The fluid injection simulation system of claim 1 wherein fluid flow resistance tactilely simulates a fluid injection procedure.

22. A method for controlling a fluid injection simulation system comprising a processing unit coupled to a variable flow resistance module, the method comprising the steps of:
    determining a fluid flow resistance that corresponds to a predetermined level of resistance; and
    controlling the variable flow resistance module to achieve a fluid flow resistance that corresponds to the predetermined level of resistance.

23. The method of claim 22 further comprising the steps of:
    measuring pressure at the variable flow resistance module; and
    estimating the fluid flow rate of the fluid flowing through the variable flow resistance module.

24. The method of claim 23 further comprising the step of modifying the fluid flow resistance based on the measured pressure.

25. The method of claim 22 wherein fluid flow resistance tactilely simulates a fluid injection procedure.

\* \* \* \* \*